US008439849B2

(12) United States Patent
Lin et al.

(10) Patent No.: US 8,439,849 B2
(45) Date of Patent: May 14, 2013

(54) INTESTINAL PERISTALSIS DETECTING DEVICE AND SYSTEM AND METHOD THEREOF

(75) Inventors: Hong Dun Lin, Taipei (TW); Yen Hsien Lee, Zhongli (TW); Mu Yu Tsai, Hsinchu (TW); Yu Jen Su, Kaohsiung (TW)

(73) Assignee: Industrial Technology Research Institute, Chutung, Hsinchu (TW)

( * ) Notice: Subject to any disclaimer, the term of this patent is extended or adjusted under 35 U.S.C. 154(b) by 192 days.

(21) Appl. No.: 12/979,536

(22) Filed: Dec. 28, 2010

(65) Prior Publication Data

US 2012/0165700 A1 Jun. 28, 2012

(30) Foreign Application Priority Data

Dec. 23, 2010 (TW) ................. 99145425 A

(51) Int. Cl.
*A61B 5/103* (2006.01)
*A61B 5/117* (2006.01)
*A61B 5/00* (2006.01)
*G06K 9/00* (2006.01)

(52) U.S. Cl.
USPC ........... 600/587; 600/309; 600/593; 382/128; 348/74; 348/77; 607/145

(58) Field of Classification Search .................. 382/128; 348/74, 77; 600/309, 587, 593; 607/145
See application file for complete search history.

(56) References Cited

U.S. PATENT DOCUMENTS

| 5,179,955 | A | 1/1993 | Levene et al. | |
|---|---|---|---|---|
| 5,227,727 | A * | 7/1993 | Segawa et al. | 324/318 |
| 5,539,312 | A * | 7/1996 | Fu et al. | 324/309 |
| 7,843,194 | B2 * | 11/2010 | Kassai | 324/309 |
| 2002/0095087 | A1* | 7/2002 | Mourad et al. | 600/442 |
| 2004/0034299 | A1* | 2/2004 | Kandori et al. | 600/409 |
| 2006/0079773 | A1* | 4/2006 | Mourad et al. | 600/438 |
| 2008/0112885 | A1* | 5/2008 | Okunev et al. | 424/9.1 |
| 2011/0050216 | A1* | 3/2011 | Stone | 324/244 |
| 2011/0054270 | A1* | 3/2011 | Derchak | 600/300 |
| 2011/0054271 | A1* | 3/2011 | Derchak et al. | 600/301 |
| 2011/0054272 | A1* | 3/2011 | Derchak | 600/301 |
| 2011/0105861 | A1* | 5/2011 | Derchak et al. | 600/301 |

FOREIGN PATENT DOCUMENTS

JP 2000262523 9/2000

* cited by examiner

*Primary Examiner* — Sean Dougherty
(74) *Attorney, Agent, or Firm* — Egbert Law Offices, PLLC

(57) ABSTRACT

An intestinal peristalsis detecting device comprises a radio frequency (RF) signal generator, an antenna, and a mixer. After the RF signal generator sends a pulse signal, the antenna receives the pulse signal and emits a pulse electromagnetic wave to an organism. Thereafter, the antenna receives a response pulse electromagnetic wave reflected from the organism to generate a response pulse signal. The mixer couples with the RF signal generator and the antenna to mix the pulse signal and the response pulse signal.

12 Claims, 8 Drawing Sheets

INTESTINAL PERISTALSIS DETECTING DEVICE AND SYSTEM AND METHOD THEREOF

TECHNICAL FIELD

The disclosure relates to a detecting device and a system and a method thereof. More particularly, the disclosure relates to an intestinal peristalsis detecting device that functions without contact and a system and a method thereof.

BACKGROUND

In a hospital or clinic, since the detection of intestinal peristalsis is applied to monitor patients' physiologic conditions after surgery, doctors or medical workers are required to regularly monitor patients' intestinal motility for tracking recovery of patients and observing for any side effects of surgery.

The current non-invasive intestinal peristalsis detecting device has several defects, including limitation to local detection only, requirement of specialized operators, and high cost. Currently, the options for clinical intestinal peristalsis detecting method include stethoscope diagnosis and ultrasonic detection. Japanese Patent No. JP 2000262523 discloses an electronic stethoscope attached to a patient's abdomen to receive sonic waves. The sonic waves can be converted by an analog/digital converter to acquire peristalsis information, based on which the medical diagnosis is made. In addition, U.S. Pat. No. 5,179,955 discloses a technique of abdominal ultrasonic wave. After the patient orally ingests micro particles, which can reflect ultrasonic wave, the device receives and processes the reflected ultrasonic wave for display. Doctors can observe the image on the display to determine the status of intestinal peristalsis.

The stethoscopic observation is not a quantification diagnosis. The ultrasonic wave is displayed to provide information about the intestinal peristalsis. Both of these techniques require contacting the detecting area for detection and need qualified medical personnel to perform procedures and assess results. Patients face risk of infection due to contact with the detecting area. Although the ultrasonic wave instrument can analyze the reflected ultrasonic wave to determine the status of the patient's intestine, the instrument is very expensive and cannot provide long-term monitoring. Moreover, because the image of the ultrasonic wave instrument needs to be assessed by a qualified doctor, the quality of the image will affect the accuracy of the assessment.

SUMMARY

An objective of the disclosure is to provide an intestinal peristalsis detecting device, and a system and method thereof. The disclosure mainly utilizes radar principles without contacting the object to detect the abdominal activity such as monitoring peristalsis before or after surgery, and thereby solves the problem of contacting the object that exists in prior arts.

Another objective of the disclosure is to provide an intestinal peristalsis detecting device and system and method thereof for long-term monitoring of patients' physiological conditions after surgery.

To achieve the above-mentioned objectives, the disclosure presents an intestinal peristalsis detecting system, which can detect an organism without contact. The intestinal peristalsis detecting system includes an intestinal peristalsis detecting device, a filter unit, and a signal processor. The intestinal peristalsis detecting device includes a radio frequency signal generator transmitting a pulse signal, an antenna, and a mixer. The antenna receives the pulse signal to emit a pulse electromagnetic wave to the organism. When the pulse electromagnetic wave is reflected, the antenna receives the reflected pulse electromagnetic wave to generate a response pulse signal. Since the mixer separately couples with both the radio frequency signal generator and the antenna, the mixer can combine the pulse signal and the response pulse signal. The filter unit filters the mixed pulse signal and the mixed response pulse signal to transmit a low-frequency signal of the pulse signal and the response signal. The signal processor coupling with the filter includes a tunable band-pass filter module and a Gaussian curve fitting module. The tunable band-pass filter module processes the low-frequency signal to separately generate an abdominal respiration signal and an abdominal activity signal. The Gaussian curve fitting module fits the abdominal activity signal according to a predetermined peristalsis pattern to determine the degree of intestinal peristalsis.

The disclosure presents an intestinal peristalsis detecting method for detecting an organism without contact. The intestinal peristalsis detecting method includes the following steps: providing a radio frequency signal generator and an antenna, wherein the radio frequency signal generator transmits a pulse signal, the antenna receives the pulse signal to emit a pulse electromagnetic wave and receive a reflected pulse electromagnetic wave to generate a response pulse signal; mixing the pulse signal and the response pulse signal; filtering the mixed pulse signal and the mixed response signal to transmit a low-frequency signal of the pulse signal and the response signal; processing the low-frequency signal to generate an abdominal activity signal and an abdominal respiration signal; and fitting the abdominal activity signal according to a predetermined peristalsis pattern to determine the degree of intestinal peristalsis.

BRIEF DESCRIPTION OF THE DRAWINGS

The accompanying drawings, which are incorporated in and constitute a part of this specification, illustrate embodiments of the disclosure and, together with the description, serve to explain the principles of the disclosure.

DETAILED DESCRIPTION

Figure 1:
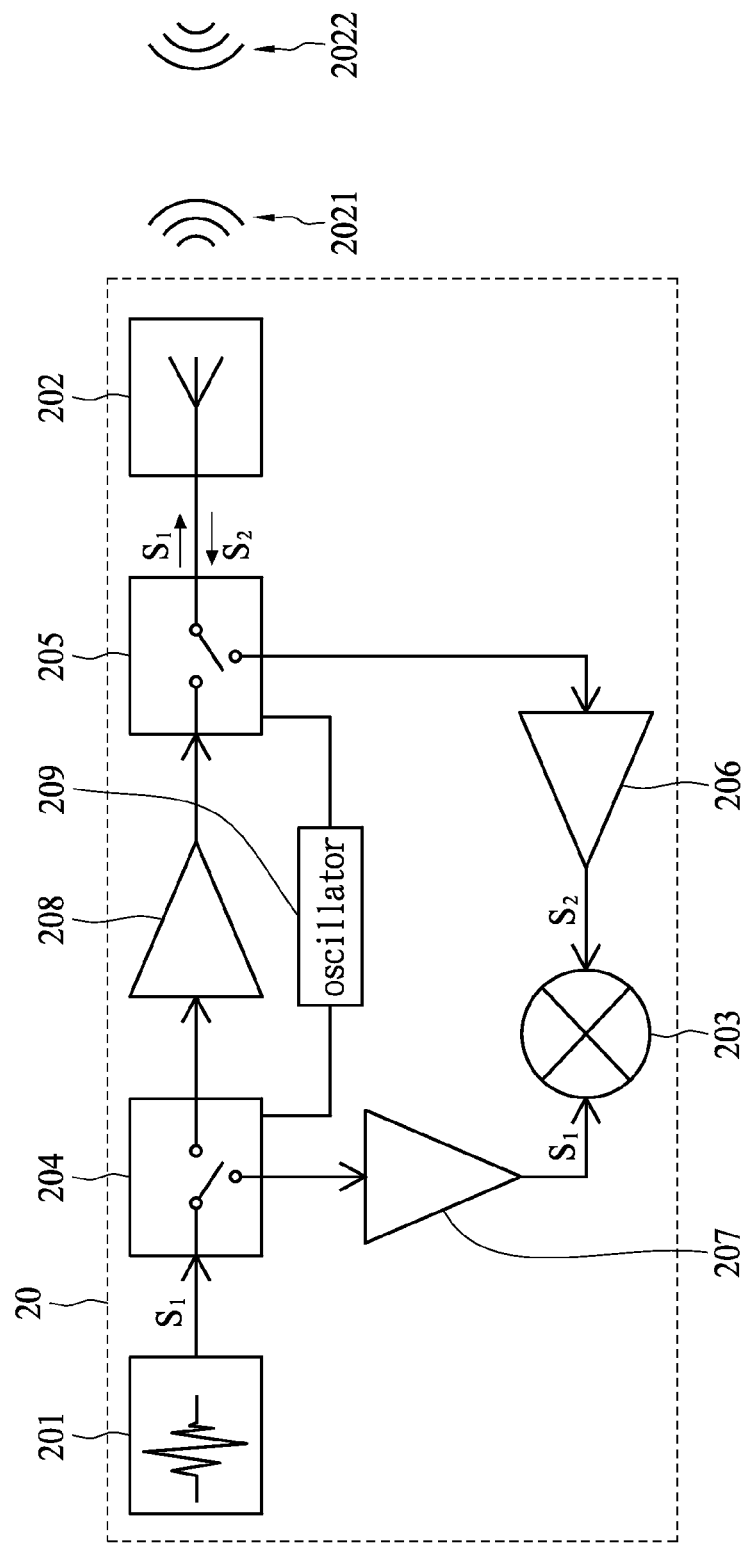
FIG. 1 shows a perspective view illustrating an intestinal peristalsis detecting device according to one exemplary embodiment of the disclosure.

Referring to FIG. 1, an intestinal peristalsis detecting device 20, which can detect an organism without contact, includes a radio frequency signal generator 201, an antenna 202, and a mixer 203. The organism preferably includes, but is not limited to, humans or other animals. The radio frequency signal generator 201 can transmit a pulse signal S1. The pulse signal preferably includes, but is not limited to, nano-second pulse signal. When the antenna 202 receives the pulse signal S1 to emit a pulse electromagnetic wave 2021 to the organism (not shown), the organism reflects a response pulse electromagnetic wave 2022, which is received by the antenna 202 to generate a response pulse signal S2. When a radially symmetrical contraction and relaxation of muscles (such as intestinal peristalsis) occurs in the organism, the intestinal peristalsis causes phase difference in the response pulse electromagnetic wave 2022 such that the intestinal peristalsis detecting device 20 can be used in near-field detection or non-contact detection of intestinal peristalsis. Generally, the intestinal peristalsis detecting device 20 is preferably, but not limited to, applied for detection of abdominal intestine activities. Since the present intestinal peristalsis detecting device 20 is a novel real-time detecting device that does not contact the detected object, the nano-second pulse near-field detecting technique in the disclosure is obviously different from the traditional ultrasonic instrument or conventional medical auscultation. Thus, the intestinal peristalsis detecting device 20 can monitor the intestinal peristalsis in real time, without contact, continuously and for long terms.

In the embodiment shown in FIG. 1, the mixer 203 separately couples with the radio frequency signal generator 201 and the antenna 202. Since the pulse signal S1 and the response pulse signal S2 can be separately transmitted to the mixer 203, and the mixer 203 can mix the pulse signal S1 and the response pulse signal S2. Particularly, the intestinal peristalsis detecting device 20 further includes a first switch 204, a second switch 205, and an oscillator 209 providing a first control frequency and a second control frequency. The first control frequency is N times the second control frequency, wherein N is a positive integer. The first switch 204 separately couples with the radio frequency signal generator 201 and the antenna 202. Based on the first control frequency, the first switch 204 transmits the pulse signal S1 to the antenna 202. In other words, the first control frequency is the frequency to control the first switch 204 to electrically couple with the antenna 202. When the first switch 204 electrically couples with the antenna 202, the pulse signal S1 will be conducted or transmitted through an amplifier 208 and the second switch 205 to the antenna 202 so as to emit a pulse electromagnetic wave 2021. In other words, the first control frequency positive correlates to the frequency of the pulse electromagnetic wave 2021. In addition, when the first switch 204 is electrically coupled with the mixer 203 according to the first control frequency, the pulse signal S1 is transmitted to the mixer 203. Thus, the first control frequency controls the frequency of the first switch 204 conducting or transmitting the pulse signal S1 to the antenna 202 or the mixer 203. The second switch 205 separately couples with the mixer 203 and the antenna 202. The second switch 205 transmits the response pulse signal S2 to the mixer 203 according to the second control frequency. In other words, the second switch 205 transmits the pulse signal S1 to the antenna 202 based on the second control frequency.

Since the first control frequency is N times the second control frequency, and N is a positive integer, the second switch 205 electrically couples with the amplifier 208 and the antenna 202 such that the first switch 204 is also electrically coupled with the radio frequency signal generator 201 and the amplifier 208 to conduct or transmit the pulse signal S1 through the first switch 204, the amplifier 208, and the second switch 205 to the antenna 202.

After the antenna 202 emits the pulse electromagnetic wave 2021 to the organism, the antenna 202 receives the response electromagnetic wave 2022 reflected from the organism to generate a response pulse signal S2. When the second switch 205 is electrically coupled with the mixer 203 based on the second control frequency, the response pulse signal S2 will be transmitted to the mixer 203. Since the first control frequency is N times the second control frequency, the first switch 204 controlled by the first control frequency partially synchronizes with the second switch 205 controlled by the second control frequency. Thus, the first switch 204 controlled by the first control frequency will be electrically coupled with the amplifier 207 to transmit the pulse signal S1 to the mixer 203. In addition, since the first control frequency positively correlates to the frequency of the pulse electromagnetic wave 2021, the increase of the first control frequency will increase amounts of the pulse signals S1 per time unit; meanwhile, the increase of the first control frequency also increases the quantity of the response pulse signals S2 per time unit. Since the quantities of the pulse signals S1 and the response pulse signals S2 per time unit increase, the intestinal peristalsis detecting device 20 can sample many signals per time unit so as to provide increased resolution of the intestinal peristalsis detecting device 20.

In the embodiment shown in FIG. 1, the intestinal peristalsis detecting device 20 further includes an amplifier 206 coupled with the second switch 205, an amplifier 207, and an amplifier 208. Since both the amplifier 207 and the amplifier 208 are coupled with the first switch 204, the amplifiers 207, 208 can amplify the pulse signal S1 passing through the amplifiers 207, 208; meanwhile the amplifier 206 can amplify the response pulse signal S2 passing through the amplifier 206.

Figure 2:
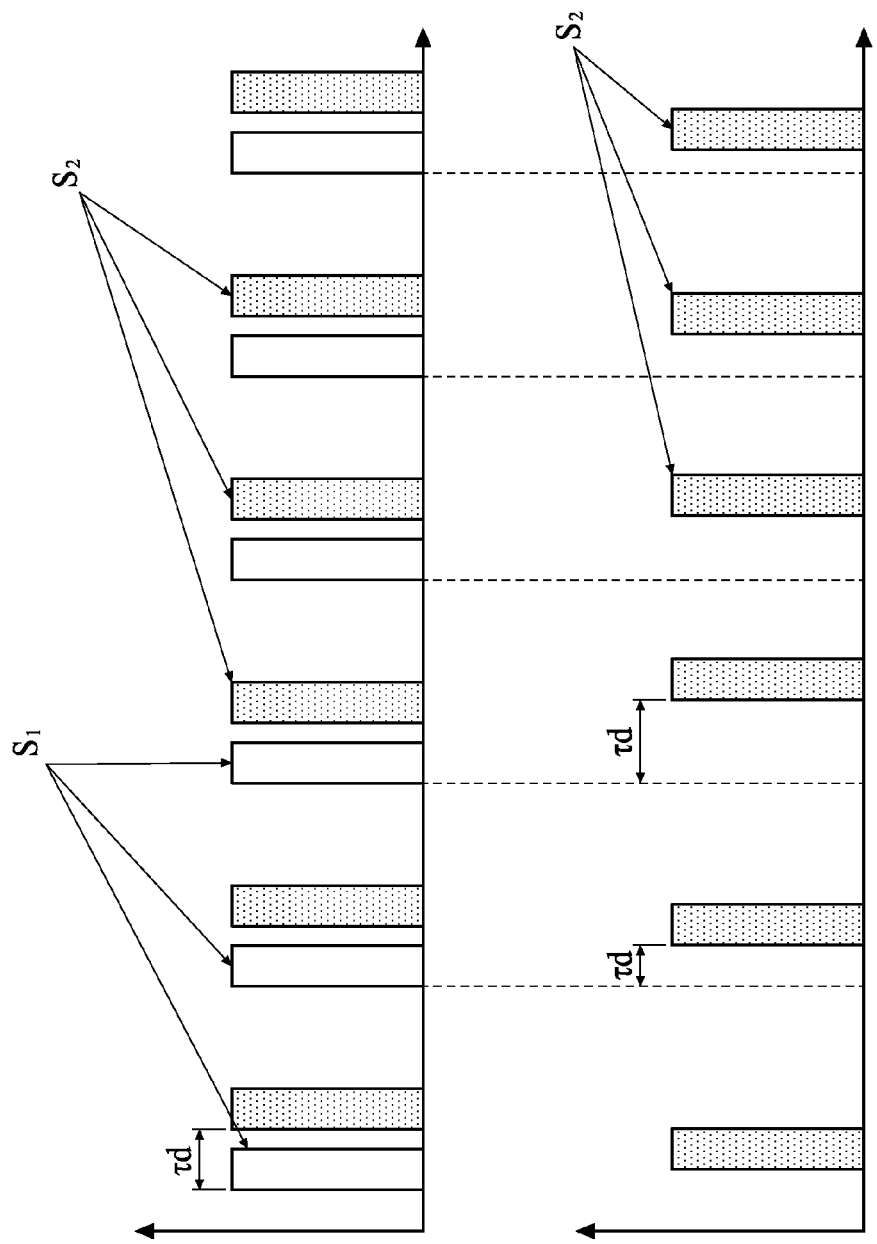
FIG. 2 shows a perspective view illustrating pulse signals S1 and response pulse signals S2 according to one exemplary embodiment of the disclosure.

As shown in FIG. 1 and FIG. 2, the working principle of the antenna 202 is to continuously emit the pulse electromagnetic wave in short pulses (of about five nanoseconds' duration) while the antenna 202 continuously receives the response pulse electromagnetic wave 2022 to generate response pulse signal S2. As shown in the upper figure of FIG. 2, if the detected object is immobile, the time interval τd between the response pulse signal S2 and the pulse signal S1 will be consistent. After being processed, the pulse signal S1 and the response pulse signal S2 can be converted into a consistent direct current. The time interval τd also indicates the phase difference between the pulse signal S1 and the response pulse signal S2. As shown in the lower figure of FIG. 2, if the detected object moves, the time interval τd between the response pulse signal S2 and the pulse signal S1 will vary according to the intensity of the signal. After being processed, the pulse signal S1 and the response pulse signal S2 can be converted into an alternating current. Therefore, the disclosure provides a nanosecond pulse near-field detecting device 20, which uses low frequency (about 1 GHz) radar principle to acquire activity information in the abdominal organs by emitting radio frequency signals and modulating received signals.

Figure 3:
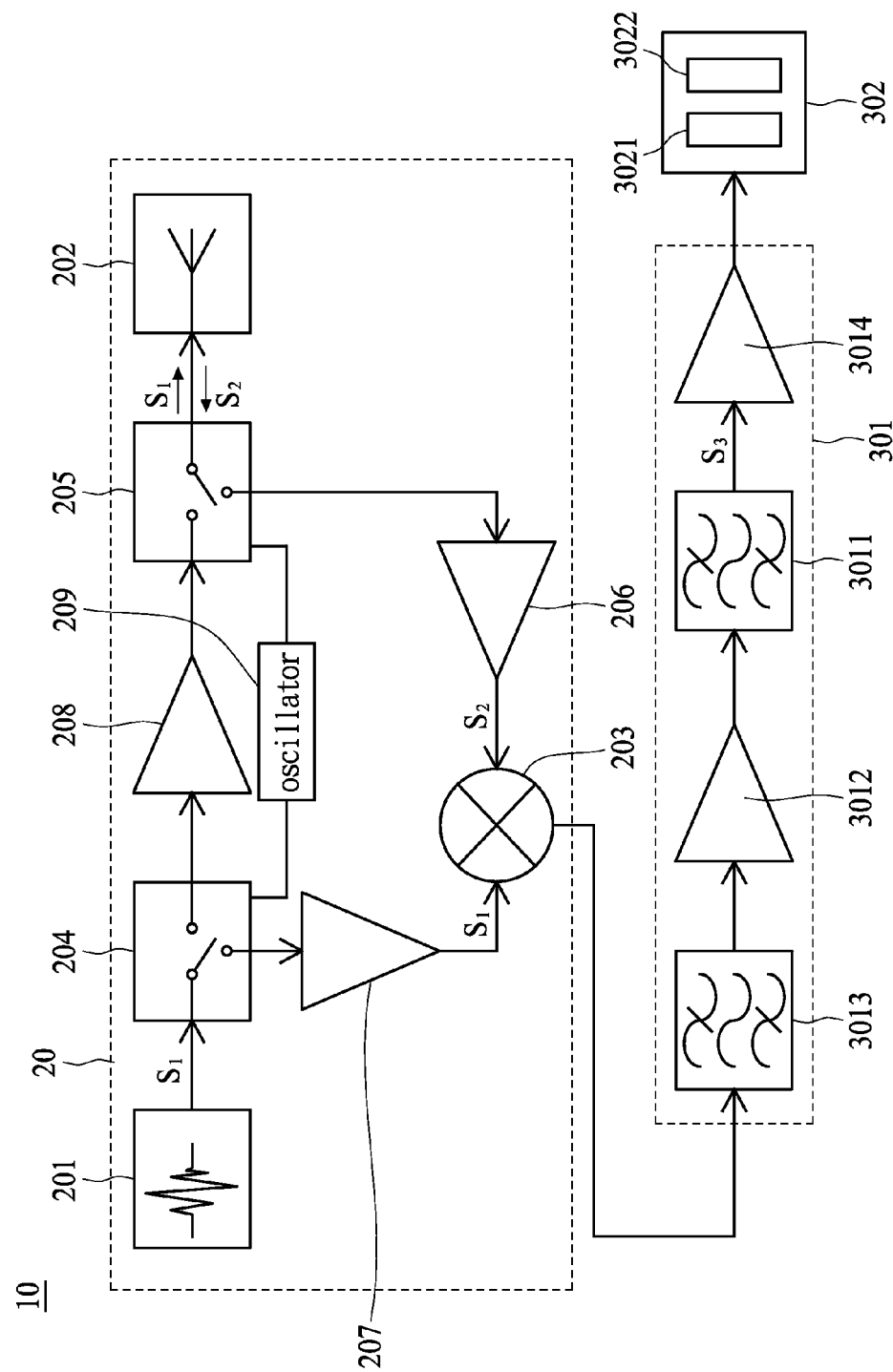
FIG. 3 shows a perspective view illustrating an intestinal peristalsis detecting system according to one exemplary embodiment of the disclosure.

FIG. 3 shows an intestinal peristalsis detecting system 10 that includes all components of the above-mentioned intestinal peristalsis detecting device 20 and further includes a filter unit 301 and a signal processor 302. The filter unit 301 filters the mixed pulse signal S1 and the mixed response pulse signal S2 to transmit a low frequency signal S3 of the pulse signal S1 and the response pulse signal S2. The low-frequency signal S3 usually ranges from 0 Hz to 0.8 Hz, and preferably ranges from 0.2 Hz to 0.1 Hz. Since the abdominal respiration signal and the abdominal activity signal mostly belong to the low-frequency signal S3, the filter unit 301 can filter out the unnecessary high-frequency (above 0 Hz to 0.8 Hz, preferably above selected low-frequence range) portion of the pulse signal S1 and the response pulse signal S2. The filter unit 301 includes a passive filter 3013, an amplifier 3012, a filter 3011, and an amplifier 3014, wherein the filter 3011 is preferably, but not limited to, a band-pass filter (0.01 to 0.8 Hz). The passive filter 3013 pre-filters the mixed pulse signal S1 and the mixed response pulse signal S2 to clean out noise in order to prevent noise due to movement of the organism or organs such as stomach peristalsis. The above-mentioned intestinal peristalsis detecting system 20 can integrate with the filter unit 301 and the passive filter 3013 to form a transceiver (not shown). The transceiver can transmit signals to the signal processor 302 via wire or wireless transmission. The transceiver and the signal processor 302 can have independent power sources, or, in another embodiment, the transceiver and the signal processor 302 can be supplied by a single power source.

The signal processor 302 can couple with the filter unit 301 via a wire system or wireless system to transmit the low-frequency signal S3. The system 10 of the disclosure integrates multiple functions including detection, signal processing, and data transmission and is portable and self-operable in a system on chip (SOC) type. In application, the system can be applied for monitoring of intestinal peristalsis after surgery and for screening for other diseases and for remote home-care service to reduce medical costs and increase the quality of medical care service.

In addition, the signal processor 302 includes a tunable band-pass filter module 3021 and a Gaussian curve fitting module 3022. Based on clinical statistical analysis and study of publication, the respiration rate of common persons ranges from 16 to 20 times per minute; the respiration rate of males ranges from 15 to 18 times per minute; the respiration rate of females ranges from 17 to 19 times per minute; the respiration rate of children ranges from 22 to 26 times per minute; the respiration rate of neonates ranges from 30 to 40 times per minute; and the intestinal peristalsis ranges from 4 to 5 times per minute. Thus, according to the clinical statistical analysis, the system 10 of the disclosure tunable band-pass filters the low-frequency signal S3. Frequency range from 0.2 Hz to 0.8 Hz retrieved from the low-frequency signal S3 is the abdominal respiration signal; meanwhile, frequency range from 0.01 Hz to 0.2 Hz retrieved from the low-frequency signal S3 is the abdominal activity signal. In summary, the tunable band-pass filter module 3021 processes the low-frequency signal S3 to generate the abdominal respiration signal and the abdominal activity signal. The Gaussian curve fitting module 3022 fits the abdominal activity signal according to a predetermined peristalsis pattern to determine the degree of intestinal peristalsis.

Figure 4:
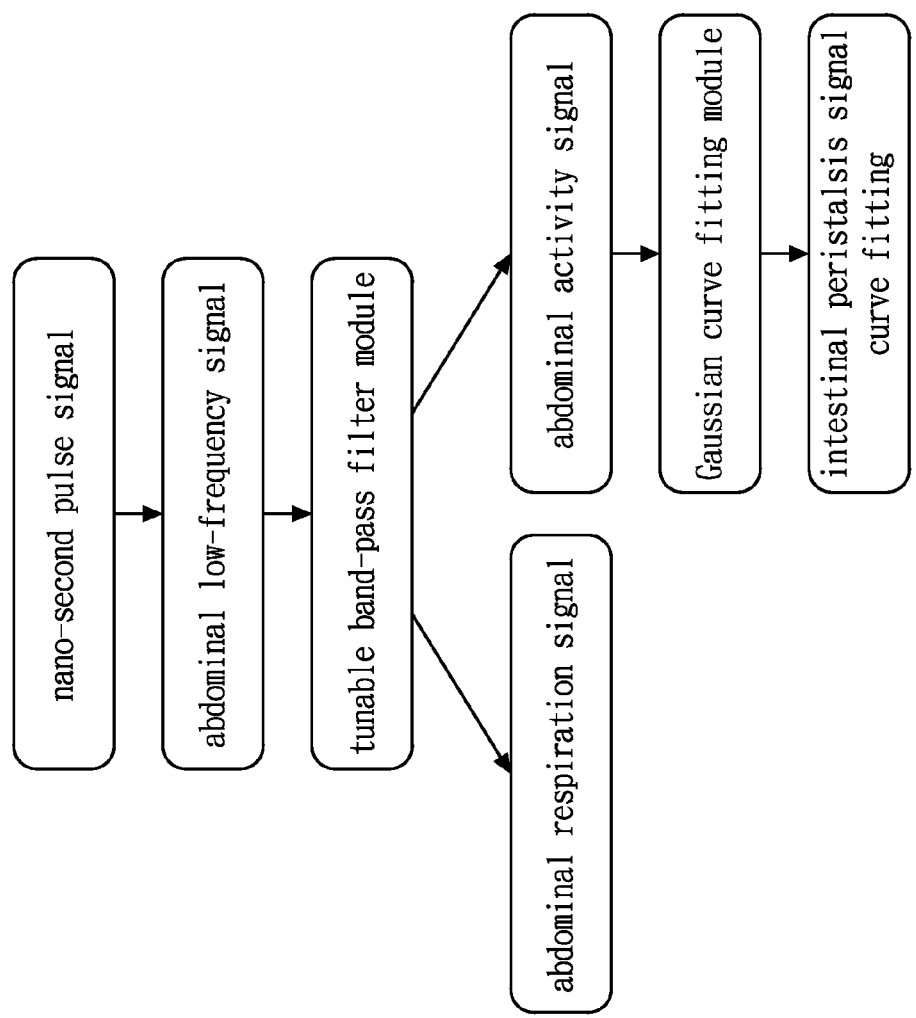
FIG. 4 shows a flow diagram illustrating a process of the pulse signals according to one exemplary embodiment of the disclosure.

As shown in FIG. 4, the disclosure utilizes the antenna of the radar principle within low frequency (about 1 GHz) to emit a pulse signal or receive a response pulse signal. The filter of the disclosure can retrieve the low-frequency signal of abdominal organs. In addition, the disclosure uses the signal processor for tunable band-pass filtering and for Gaussian curve fitting the abdominal respiration signal and the abdominal activity signal in order to achieve the object of detecting the intestinal peristalsis signal in the abdomen.

Figure 5A:
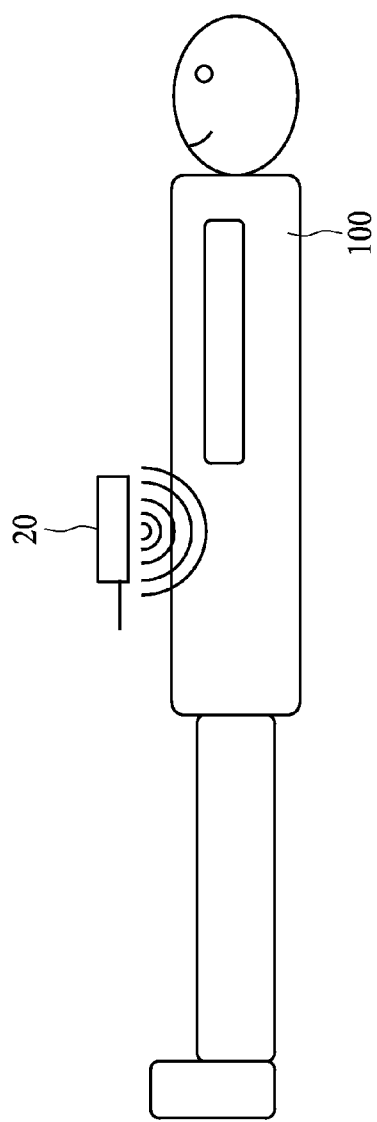
FIG. 5A shows a side view illustrating a condition of the intestinal peristalsis detecting device according to one exemplary embodiment of the disclosure.
Figure 5B:
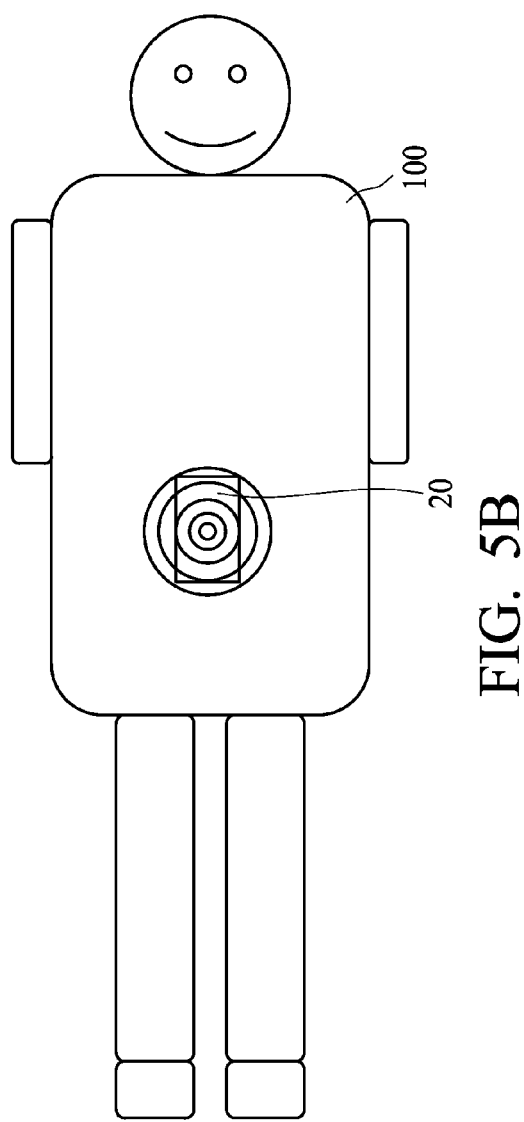
FIG. 5B shows a top view illustrating a condition of the intestinal peristalsis detecting device according to one exemplary embodiment of the disclosure.
Figure 6:
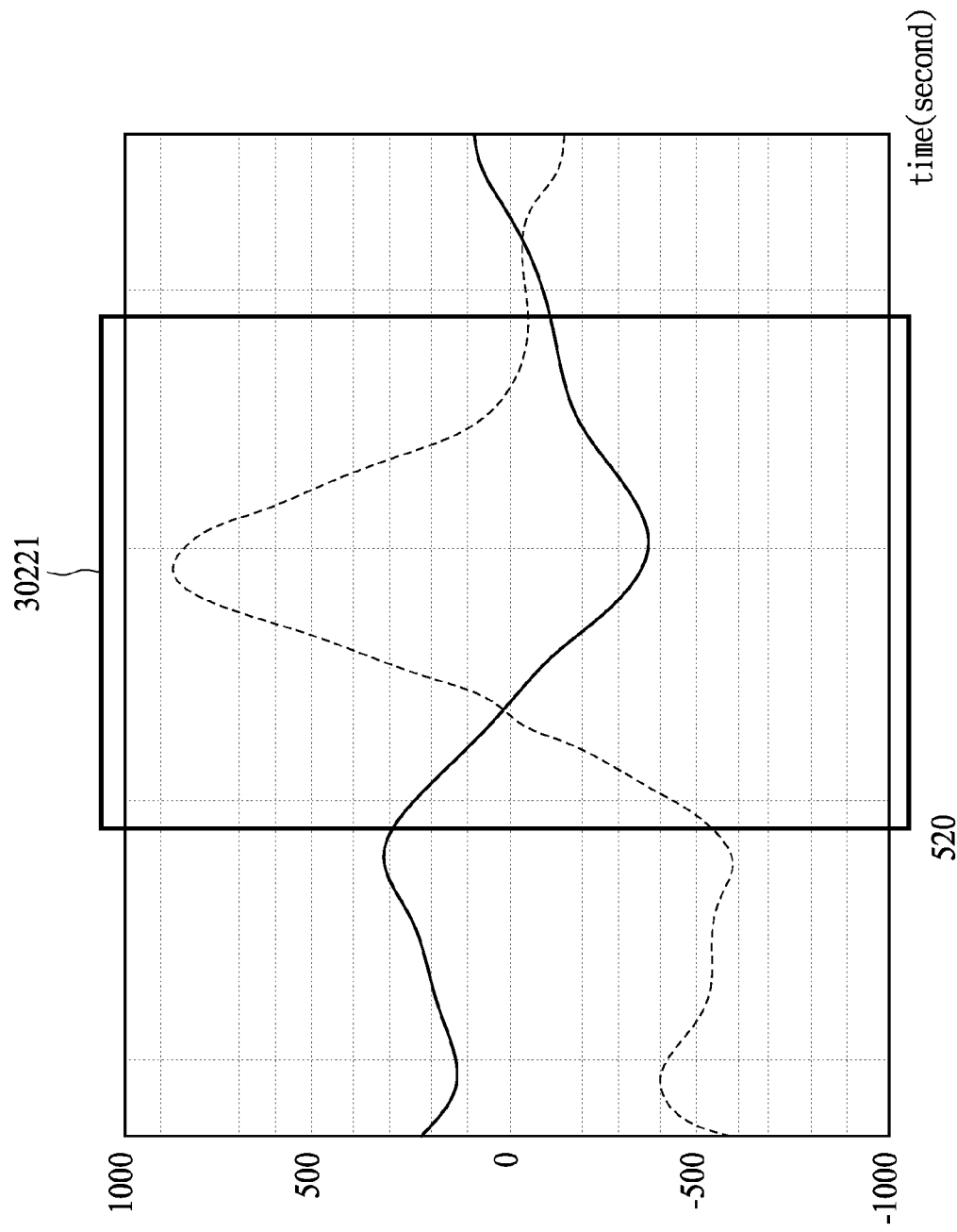
FIG. 6 shows a perspective view illustrating Gaussian curve fitting according to one exemplary embodiment of the disclosure.

As shown in FIG. 5A and FIG. 5B, the intestinal peristalsis detecting device 20 detects the abdomen of humans 100 without contact. The intestinal peristalsis detecting device 20 is disposed about 10 centimeters above the detecting area such as the navel. The detecting area is a round area with a diameter of 5 cm. FIG. 6 shows the intestinal peristalsis detecting device 20 utilizing Gaussian curve fitting to fit the abdominal activity signal according to a predetermined peristalsis pattern so as to determine the degree of intestinal peristalsis. In particular, when the predetermined peristalsis pattern 30221 fits the abdominal activity signal, every fit counts one occurrence of intestinal peristalsis. The predetermined peristalsis pattern 30221 is an exemplary embodiment of, but not limited to, the pattern shown in FIG. 6.

Figure 7:
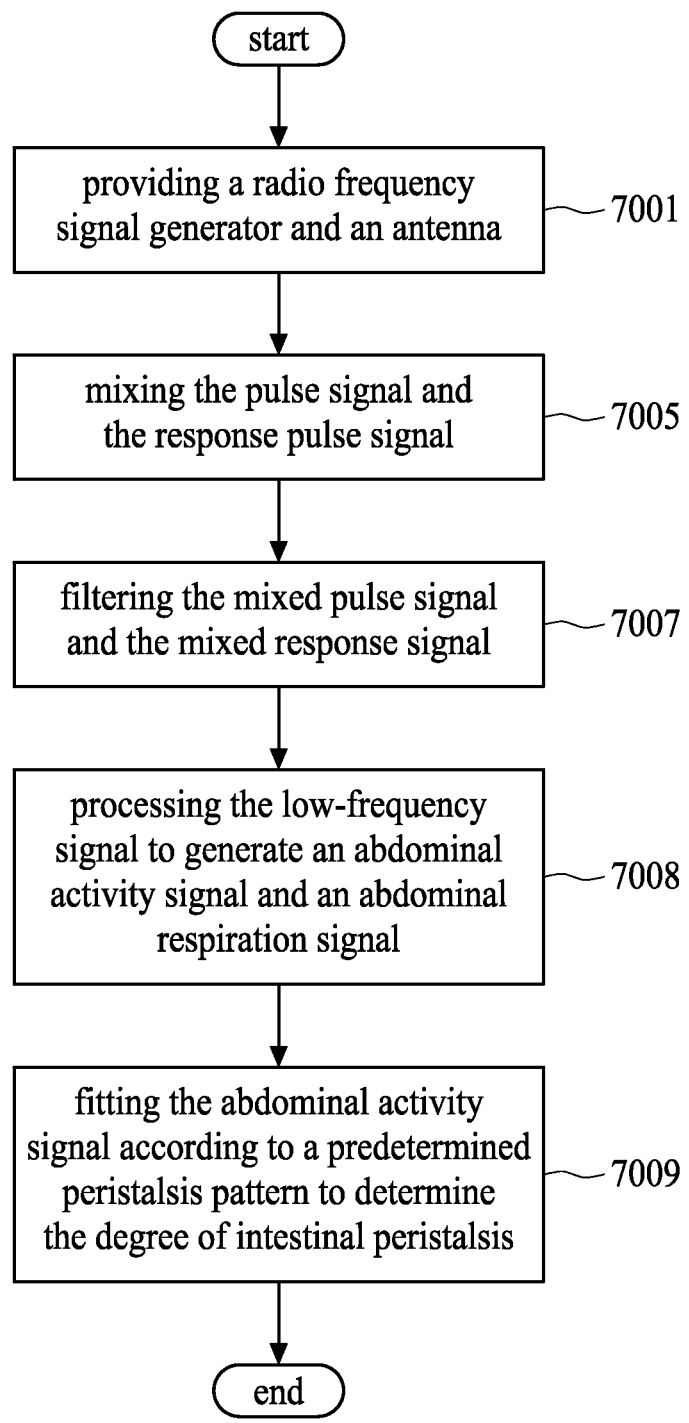
FIG. 7 shows a flow diagram illustrating an intestinal peristalsis detecting method according to one exemplary embodiment of the disclosure.

FIG. 7 shows an intestinal peristalsis detecting method comprising the following steps: step 7001 provides a radio frequency signal generator and an antenna, wherein the radio frequency signal generator transmits a pulse signal, and the antenna receives the pulse signal to emit a pulse electromagnetic wave and receives a response pulse electromagnetic wave to generate a response pulse signal; step 7005 mixes the pulse signal and the response pulse signal; step 7007 filters the mixed pulse signal and the mixed response pulse signal to generate a low-frequency signal of the pulse signal and the response pulse signal; step 7008 processes the low-frequency signal to generate an abdominal respiration signal and an abdominal activity signal; and step 7009 fits the abdominal activity signal according to a predetermined peristalsis pattern to determine the degree of intestinal peristalsis.

Figure 8:
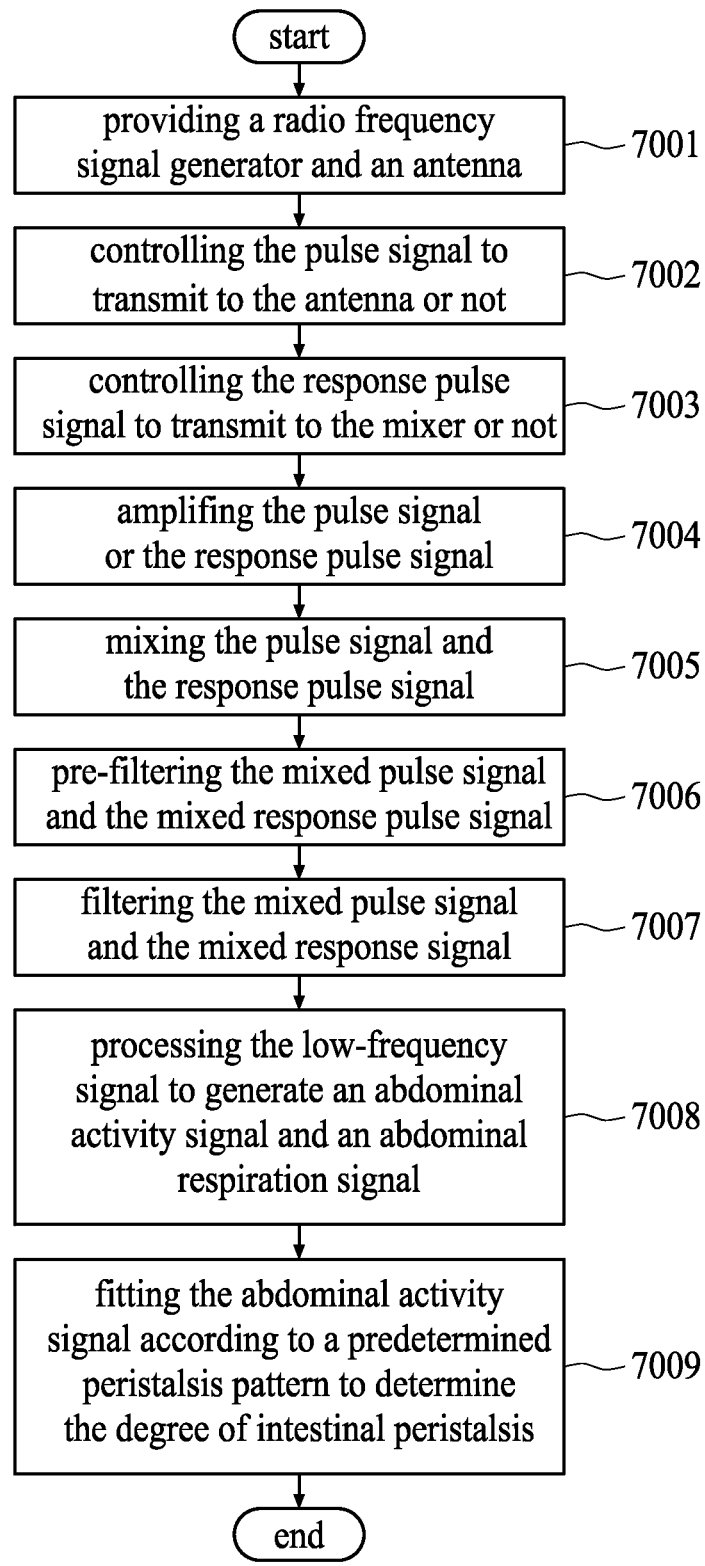
FIG. 8 shows a flow diagram illustrating an intestinal peristalsis detecting method according to another exemplary embodiment of the disclosure.

As shown in FIG. 8, the intestinal peristalsis detecting method further comprises step 7002, which determines whether the pulse signal is to be transmitted to the antenna; step 7003, which controls whether the response pulse signal is to be transmitted to the mixer; step 7004, which amplifies the pulse signal or the response pulse signal; and step 7006, which pre-filters the mixed pulse signal and the mixed response pulse signal to clean out noise.

The above-described exemplary embodiments are intended to be illustrative only. Those skilled in the art may devise numerous alternative embodiments without departing from the scope of the following claims.

What is claimed is:

1. An intestinal peristalsis detecting device, for detecting an organism without contact, the intestinal peristalsis detecting device comprising:
   a radio frequency signal generator for transmitting a pulse signal;
   an antenna for receiving the pulse signal so as to emit a pulse electromagnetic wave in response to the pulse signal, said antenna for receiving a reflected pulse electromagnetic wave to generate a response pulse signal in response to the reflected pulse electromagnetic wave; and
   a mixer coupled with the radio frequency signal generator and the antenna for mixing the pulse signal and the response pulse signal, wherein the pulse signal and the response pulse signal have a phase difference.

2. The intestinal peristalsis detecting device of claim 1, further comprising a first switch separately coupling with the radio frequency signal generator and the antenna, wherein the first switch transmits the pulse signal to the antenna according to a first control frequency, and wherein the first control frequency is positively correlated with the frequency of the pulse electromagnetic wave emitted from the antenna.

3. The intestinal peristalsis detecting device of claim 2, further comprising a second switch; separately coupling with the mixer and the antenna, wherein the second switch transmits the response pulse signal to the mixer according to a second control frequency, and wherein the second switch transmits the pulse signal to the antenna according to the second control frequency.

4. The intestinal peristalsis detecting device of claim 3, further comprising an oscillator for providing the first control frequency and the second control frequency, wherein the first control frequency is N times the second control frequency, and N is a positive integer.

5. The intestinal peristalsis detecting device of claim 3, further comprising at least one amplifier coupled with the first switch or the second switch for amplifying the pulse signal or the response pulse signal passing through the amplifier.

6. An intestinal peristalsis detecting system for detecting an organism without contact, the intestinal peristalsis detecting system comprising:
    an intestinal peristalsis detecting device comprising:
        a radio frequency signal generator for transmitting a pulse signal;
        an antenna for receiving the pulse signal to emitting a pulse electromagnetic wave in response to the pulse signal and for receiving a reflected pulse electromagnetic wave, said antenna for generating a response pulse signal in response to the reflected pulse electromagnetic wave; and
        a mixer coupled with the radio frequency signal generator and the antenna, for mixing the pulse signal and the response pulse signal;
    a filter unit for filtering the mixed pulse signal and the mixed response pulse signal to transmit a low-frequency signal of the pulse signal and the response signal; and
    a signal processor coupled with the filter unit, the signal processor comprising:
        a tunable band-pass filter module for processing the low-frequency signal to generate an abdominal activity signal; and
        a Gaussian curve fitting module for fitting the abdominal activity signal according to a predetermined peristalsis pattern to determine the degree of intestinal peristalsis.

7. The intestinal peristalsis detecting system of claim 6, wherein the intestinal peristalsis detecting device further comprises a first switch separately coupled with the radio frequency signal generator and the antenna, wherein the first switch transmits the pulse signal to the antenna according to a first control frequency, and the first control frequency is positively correlated with the frequency of the pulse electromagnetic wave emitted from the antenna.

8. The intestinal peristalsis detecting system of claim 7, wherein the intestinal peristalsis detecting device further comprises a second switch separately coupled with the mixer and the antenna, wherein the second switch transmits the response pulse signal to the mixer according to a second control frequency, and the second switch transmits the pulse signal to the antenna according to the second control frequency.

9. The intestinal peristalsis detecting system of claim 8, further comprising an oscillator for providing the first control frequency and the second control frequency, wherein the first control frequency is N times the second control frequency, and N is a positive integer.

10. The intestinal peristalsis detecting system of claim 8, wherein the intestinal peristalsis detecting device further comprises at least one amplifier coupled with the first switch or the second switch for amplifying the pulse signal or the response pulse signal passing through the amplifier.

11. The intestinal peristalsis detecting system of claim 8, wherein the filter unit further comprises a passive filter coupled with the mixer, the passive filter for pre-filtering the mixed pulse signal and the mixed response pulse signal to clean out noise.

12. An intestinal peristalsis detecting method for detecting an organism without contact, the intestinal peristalsis detecting method comprising the following steps:
    providing a radio frequency signal generator and an antenna, wherein the radio frequency signal generator transmits a pulse signal and the antenna receives the pulse signal, the antenna emitting a pulse electromagnetic wave in response to the pulse signal the antenna receiving a reflected pulse electromagnetic wave, the antenna generating a response pulse signal in response in response to the reflected pulse electromagnetic wave;
    mixing the pulse signal and the response pulse signal;
    filtering the mixed pulse signal and the mixed response signal and transmitting a low-frequency signal of the pulse signal and the response pulse signal;
    processing the low-frequency signal to generate an abdominal activity signal; and
    fitting the abdominal activity signal according to a predetermined peristalsis pattern to determine the degree of intestinal peristalsis.

\* \* \* \* \*